United States Patent
Joshi et al.

[19]

[11] Patent Number: 5,538,605
[45] Date of Patent: Jul. 23, 1996

[54] SOLID OXIDE CATHODE-BASED ELECTROCHEMICAL OXYGEN GENERATOR FOR FLUID DISPENSING APPLICATIONS

[75] Inventors: Ashok V. Joshi; John H. Gordon, both of Salt Lake City, Utah

[73] Assignee: Ceramatec, Inc., Salt Lake City, Utah

[21] Appl. No.: 300,947

[22] Filed: Sep. 6, 1994

[51] Int. Cl.$^6$ .............. C25B 9/00; C25B 13/08; C25B 15/08
[52] U.S. Cl. .............. 204/266; 204/271; 204/296
[58] Field of Search .............. 204/266, 296, 204/271, 252

[56] References Cited

U.S. PATENT DOCUMENTS

| | | | |
|---|---|---|---|
| 3,996,126 | 12/1976 | Rasmussen | 204/271 |
| 5,186,805 | 2/1993 | Gross et al. | 204/266 X |
| 5,242,565 | 9/1993 | Winsel | 204/266 X |
| 5,395,501 | 3/1995 | Rohrbacher et al. | 204/266 X |
| 5,423,454 | 6/1995 | Lippman | 204/271 X |

*Primary Examiner*—Donald R. Valentine
*Attorney, Agent, or Firm*—Trask, Britt & Rossa

[57] ABSTRACT

A self-contained, gas-generating electrochemical cell has been invented. The cell contains an anode which is exposed to water or water containing material, a water permeable, ion-conducting separator between the anode from the cathode and a cathode composed of an electrochemically decomposable chemical compound which produces water in the presence of protons and electrons.

An exemplary cell contains silver oxide as a principal component of the cathode, water as the principal anode component and a proton conducting membrane. The silver oxide reacts with protons electrically driven through said membrane and electrons from a power-source to form elemental silver and water. Deposition of elemental silver in the cathode compartment is advantageous inasmuch as it improves the electronic conductivity of the material in the cathode compartment. Water, in the anode, decomposes to protons and molecular oxygen while releasing electrons. It is this oxygen which acts as a pressurizing gas to perform some useful work, such as being the motive force to dispense fluids from a fluid-containing bladder to deliver said dispensed fluids to a particular site. The dispensed fluids may have some beneficial property such as medicinal, insecticidal, fragrant or other attributes.

10 Claims, 4 Drawing Sheets

SOLID OXIDE CATHODE-BASED ELECTROCHEMICAL OXYGEN GENERATOR FOR FLUID DISPENSING APPLICATIONS

BACKGROUND OF THE INVENTION

1. Field of the Invention

The invention relates to a self-contained, gas-generating, electrochemical cell. The invention further relates to a dispensing device, in particular a device where oxygen gas released from a solid state electrochemical cell increases in pressure to press fluid from a bladder within a chamber through an outlet of the device in a steady continuous flow until the fluid contents of the bladder are exhausted.

2. State of the Art

Richter in U.S. Pat. No. 3,894,538 disclosed a device for dispensing medicines to man or beast. The medicine was contained in a flexible container which became compressed as fluid was electro-osmotically introduced into an adjacent flexible chamber or when gas was electrolytically produced using precious metal electrodes and an unspecified fixed electrolyte. The rate of medicine discharge was to be regulated using a potentiometer.

Maget in U.S. Pat. No. 4,522,698 disclosed electrochemical prime movers. Embodiments of the invention include a device for dispensing pharmaceuticals to a human body over a substantial period of time at a sustained very low rate, where a battery provides the driving force to transport an electrochemically active gas from a precharged chamber to a second chamber, where an ion-exchange membrane separates the two chambers; or where the battery provides the driving force to transport oxygen from air across an ion-exchange membrane to a chamber. Pressure in a chamber increases as electroactive gas transports across the membrane, this increase in pressure drives a piston which forces the contained pharmaceutical fluid to flow through an outlet. The invention requires electrodes which are electrically conductive and act as catalyst to convert molecules to ions; titanium-palladium alloy or palladium black are recommended materials. A controller is utilized to control the magnitude and time pattern of current and voltage applied to the membrane as well as to turn current on and off. To function, the invention requires either exposure to air or precharging with an electroactive gas.

Maget in U.S. Pat. No. 4,886,514 disclosed electrochemically driven drug dispensers. A potential from an external power source drives an electrochemically active gas such as hydrogen or oxygen to be transported across a membrane from a fixed volume chamber to a chamber which has a variable volume. The volume of the chamber varies by either flexing an expansible diaphragm type wall or by displacing a sliding wall, said wall is shared by a second variable volume chamber which contains a fluid drug to be administered. As the electrochemically active gas is transported to the first variable volume chamber, the drug is forced out of the second variable volume chamber through an outlet. Countering the electrochemical transport of gas across the membrane, the gas diffuses in the opposite direction across the membrane in accordance to the pressure gradient and diffusivity properties of the membrane. A controller compensates for the gas diffusion rate and varies the voltage and current to achieve the desired drug delivery rate in a steady or intermittent mode. To function, the invention requires precharging with an electroactive gas.

Maget et al. in U.S. Pat. No. 4,902,278 disclosed a fluid delivery micropump. The pump utilizes an air-actuated battery in a fixed closed circuit with an electrochemical cell which drives the transport of oxygen in air across a membrane. The transport applies external pressure to a collapsible reservoir filled with fluid, as a result, fluid is expelled from the reservoir through an outlet. The membrane is preferably a Nafion material (a perfluoro sulfonic polymer) which has been coated with platinum black/10% Teflon. Electrodes are preferably titanium screens. To control the current, a resistor is utilized. The device is activated by removing a protective peel tab to expose air inlet ports to the battery cathode. A disadvantage of this type of system is that shelf life of the device is dependent on the integrity of the seals which prevent air leakage to the battery. If the seals are not perfect, the battery will slowly discharge before the desired time of use. To function, the invention requires exposure to air.

Winsel in U.S. Pat. No. 5,242,565 disclosed "a device for electrochemical generation of gases for the transportation of fluids and similar mediums." Winsel discloses two approaches. In one approach, the device is constructed very similar to a zinc-air battery. To function, the device must be operated in total absence of oxygen, then it will release hydrogen in a controlled manner. This approach has two disadvantages: 1) in many applications hydrogen is undesirable to collect because it is difficult to contain in a flexible bladder and also is flammable, 2) maintaining an oxygen-free condition is very difficult since most flexible bladder materials are somewhat permeable to oxygens. The other approach which is disclosed by Winsel again is similar to a zinc-air battery except that instead of zinc in the cathode, a reducible oxide or nitrate is present with an alkaline electrolyte. This approach has the advantage that oxygen is released instead of hydrogen; however, cells with alkaline electrolytes are difficult to seals thus a safety hazard may be present or unreliability may result. A description of and explanation for alkaline electrolyte creepage are presented in "Why Alkaline Cells Leak," M. Hull and H. James; J. Electrochem. Soc., March 1977, pp. 332–339.

The prior art includes several devices which are capable of performing the general function of the device presently disclosed; however, the prior art has not satisfied a demand which exists for a device which 1) has a design which can dispense a fluid over a nearly constant rate for an extended period of time, 2) has a simple design which is conducive to fabrication, 3) does not require exposure to air, fluid or the precharging of an electrochemically active gas to fiction.

The present device disclosed is particularly distinguished from the prior art in that the device can function while completely sealed from its external environment, excluding the outlet port through which the fluid will be dispensed and without requiring an internal reservoir of gas to be pumped. Although an organic ion-exchange membrane is utilized in this device, this device is less sensitive to changes in ambient humidity because the membrane is sealed from the environment. Also, the device does not rely on access to air or other gas to operate nor must precautions be taken to avoid the presence of particular gases such as oxygen. The present device also does not utilize an alkaline electrolyte and is distinguished frown the prior art where such electrolyte is difficult to contain. The present device may utilize an electrolyte which is substantially neutral in pH or only slightly acidic, thus posing a reduced safety threat in the event that the contents were released. Further, because the device is simply structured and is comprised of readily available, easily fabricated materials, it is disposable.

SUMMARY OF INVENTION

A self-contained, gas-generating electrochemical cell has been invented. The cell contains an anode which is exposed to water or water containing material, a water permeable, ion-conducting membrane or separator and a cathode composed of an electrochemically decomposable chemical compound which produces water in the presence of protons and electrons.

An exemplary cell contains silver oxide as a principal component of the cathode, an anode consisting of electroconductor and electrocatalyst suitable for evolution of oxygen, and a proton conducting separator. The silver oxide reacts with protons electrically driven through said membrane and electrons from a power-source to form elemental silver and water. Deposition of elemental silver in the cathode compartment is advantageous inasmuch as it improves the electronic conductivity of the material in the cathode compartment. Water, exposed to the anode, decomposes to protons and molecular oxygen while releasing electrons. It is this oxygen which acts as a pressurizing gas to perform some useful work, such as being the motive force to dispense fluids from a fluid-containing bladder to deliver said dispensed fluids to a particular site. The dispensed fluids may have some beneficial property such as medicinal, insecticidal, fragrant or other attributes.

DETAILED DESCRIPTION OF INVENTION

In an exemplary cell, the cathode chamber may contain water (a small amount) and silver oxide ($Ag_2O$). A gelling or suspension agent, for example, carboxymethyl cellulose and the like may be desirable to improve manufacturability but is not otherwise required. Also, dispersed solid polymer electrolyte may be added to the cathode material. For example, 5% Nation solution may be added to the oxide then dried, leaving a mixture which is easily pelletized and which conducts protons. The anode chamber contains water.

The reaction at the cathode is:

1) $Ag_2O + 2H^+ + 2e^- \rightarrow 2Ag + H_2O$ The reaction at the anode is:

2) $H_2O \rightarrow \frac{1}{2}O_2 + 2H^+ + 2e^-$

The hydrogen ions produced in the anode compartment are electrically transported through the membrane to react with $Ag_2O$ in the cathode chamber to produce elemental silver and water. The water permeates (migrates) through the membrane from the cathode compartment to be available in the anode compartment to undergo dissociation.

In the instant situation, $Ag_2O$ reacts with a proton to form water, which is an effective proton conductor under appropriate conditions. Metallic silver, which is an excellent electronic conductor, will tend to plate out upon the cathode chamber wall in contact with the negative pole of the power source (battery) thereby improving the electronic conductivity of the cathode compartment material.

Figure 1:
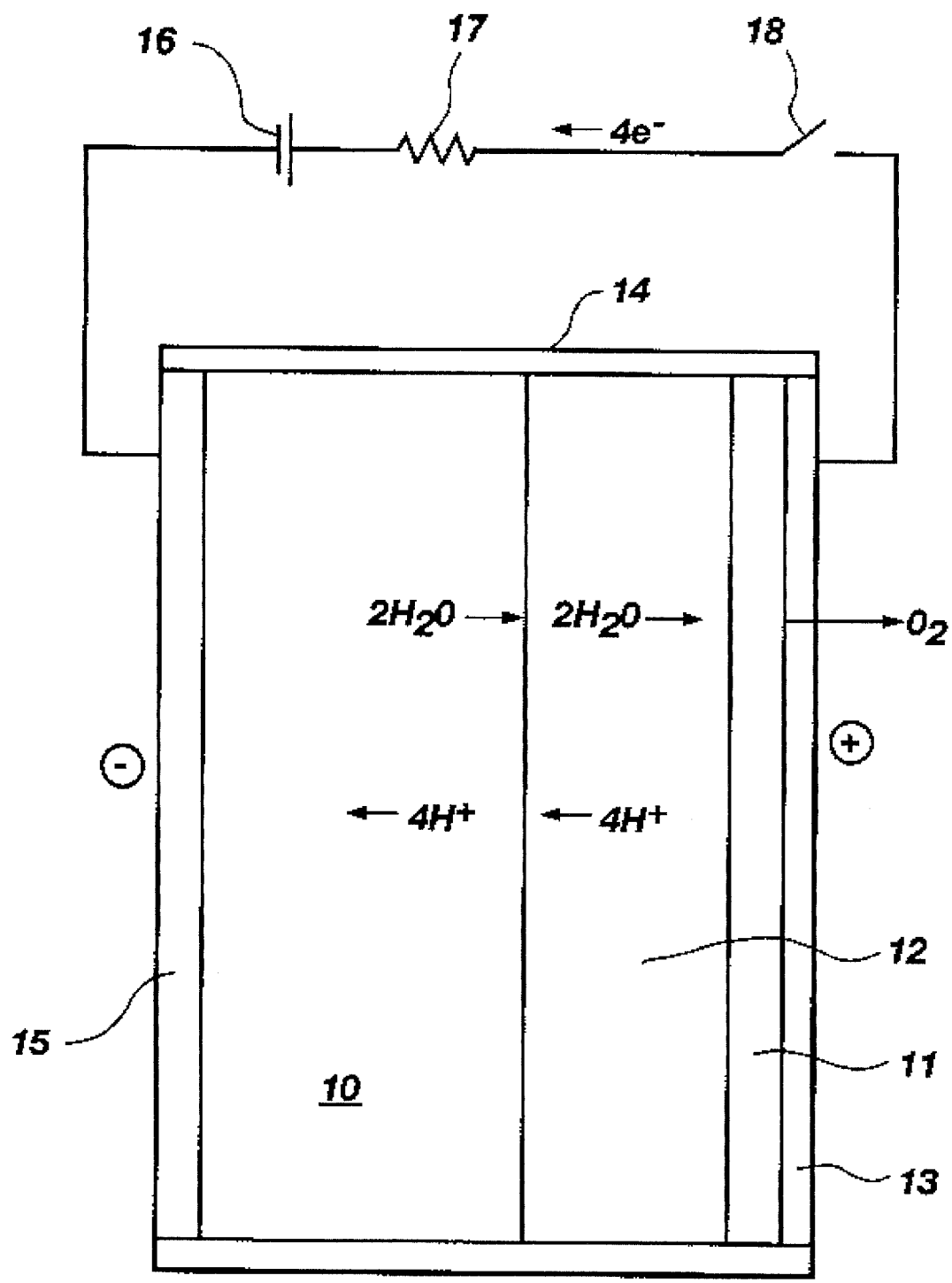
FIG. 1 is a schematic of the gas-generating, self-contained electrochemical cell employing a decomposable, proton-consuming, water-producing, chemical compound as a cathode material.

The device schematically illustrated in FIG. 1 is particularly advantageous inasmuch as the gas-generating cell can be readily sealed and completely isolated from the external environment. The cathode 10 and anode 11 chambers and the membrane separator 12 can be an integral unit which may be readily fabricated. The battery 13, power source, in contrast to many previous devices, can be external to the cell so long as it is in the electrical circuit between the anode and cathode. Thus, by sealing the perimeters or boundaries of the cathode and anode compartments to each other or to the electrolyte (membrane) a compact, sealed cell is readily produced. Of course, if the compartment shells are sealed to one another an electrical insulator must be used as part of the seal so that the cathode and anode materials are electrically isolated from one another except through the membrane and external circuit.

The cell employs a separator which has no electronic conductivity but is permeable to both protons and water. Several materials can serve this purpose. Many examples are well known in the battery industry. Hydrophilic microporous membranes made of polystyrene, polyolefin or glass fibers can absorb enough water or acid so that they are permeable to both water and protons yet are substantially electronic insulators. The cell may also employ a cation exchange membrane which is permeable to protons and water. An example of such a membrane is Nafion™, a sulfonated perfluoroethylene polymer produced by Dupont, other sulfonated polymers are well known in the art. A gas permeable anode is adhered to the separator or membrane. The oxygen evolving anode must communicate with a flexible gas chamber into which the oxygen flows. A cathode chamber contains a catholyte of water, a metal oxide such as $Ag_2O$, $CuO$, $Cu_2O$, $PbO_2$, $PbO$, $ZnO$, $Bi_2O_3$ and the like, and possibly, a gel forming material such as carboxymethyl cellulose and the like to improve manufacturability. A battery is in direct contact with its negative pole in contact with the cathode. The positive pole of the battery is connected to a switch in a conductor circuit, which upon activation completes a circuit with the anode.

Although water is not necessary to initiate the cathode reaction, some small amount of water is generally desirable to assist in the ionic conductivity of the separator or membrane and catholyte. As protons migrate through the electrolyte, the cathode reaction produces water, which permeates through the membrane to replace water at the anode which decomposes to produce gaseous oxygen.

Oxygen generated at the anode may be directed to a dispensing chamber wherein the oxygen gas compresses a bladder to force out fluid contained in the bladder to be delivered to a desired site.

FIG. 1 is a schematic of the gas-generating, self-contained electrochemical cell employing a decomposable, proton-consuming, water-producing, chemical compound as a cathode material. The membrane material 12 is either a cation exchange membrane or is a microporous membrane which is permeable to both water and cations, in particular protons. The anode 11 is composed of electronic conductors, e.g., graphite and the like, and electrocatalyst material suitable for oxidation of water to oxygen and protons in an acidic media. Examples of suitable electrocatalyst would be Ru, $RuO_2$, Ir, $IrO_2$, and combinations thereof.

Several electrodes are available which may be utilized to evolve oxygen at the anode. They are disclosed in the article "Bifunctional electrodes for an integrated water-electrolysis and hydrogen-oxygen fuel cell with a solid polymer electrolyte," J. Ahn & R. Holze, J. Applied Electrochemistry 22 (1992) 1167–1174; and in U.S. Pat. No. 4,039,409, LaConti et al. The information in these references is incorporated herein by reference.

The anode 11 must also be permeable to water molecules and protons and to oxygen. Gaseous oxygen is produced at the anode/membrane interface. The current collector 13 may serve as the anode provided that the anode surface facing the membrane has channels through which the generated oxygen can escape and provided that a means exists for water and protons to reach the anode. A film of water between the membrane and anode would serve this purpose. An electronically conductive screen coated with an appropriate electrocatalyst could also serve as an anode.

The cell shell 14 and cathode current collector 15 are impervious to gases and water so that the only transport of material into or out of the cell is through the anode current collector which is either porous or has at least one perforation through which evolved oxygen can escape. The shell can be integrated with other components such as the anode current collector, but the cathode current collector and anode current collector must be electronically isolated except through the circuit as shown with includes, at a minimum, a switch 18 and usually will also include a DC power source such as a battery 16 and a resistor 17 which is selected to attain a desired gas generation rate. In some cases such as when AgO is the active cathode material, a battery may be unnecessary.

Figure 2:
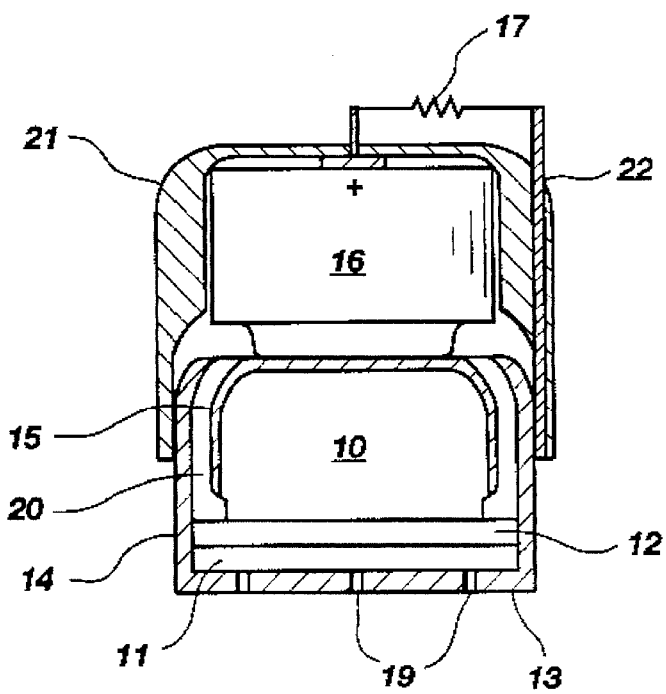
FIG. 2 is a schematic of the gas-generating, self-contained electrochemical cell as shown in FIG. 1 which has been integrated with a battery power source.

FIG. 2 is a cross-sectional view of a gas-generating, self-contained electrochemical cell of the type schematically shown in FIG. 1 which has been integrated with a battery power source 16. The shell 14 has been integrated with the anode current collector 13 to form a "can" which has at least one hole, i.e. oxygen port 19, perforated through one end and is open at the other end to accept other components during manufacturing. An insulative grommet 20 has been introduced to isolate the can from the cathode current collector. A battery retainer 21 holds the battery and includes terminals 21 and 22 which, respectively, contact the positive contact of the battery and the side of the anode current collector "can", i.e. shell 14. A resistor 17 is positioned between the two contact terminals. The device is activated when the battery retainer is slid over the "can" such that the negative contact of the battery communicates with the cathode current collector, and the anode terminal 22 communicates with, i.e. contacts, the anode "can" 14. The anode terminal may be fixed to the battery retainer or it can slide within a groove (not shown) in the sidewall of the retainer so that the retainer can be slid over the can without necessarily completing the electrical circuit until the anode terminal is slid downward to contact the can (anode current collector 13) to complete the electrical circuit.

Figure 3:
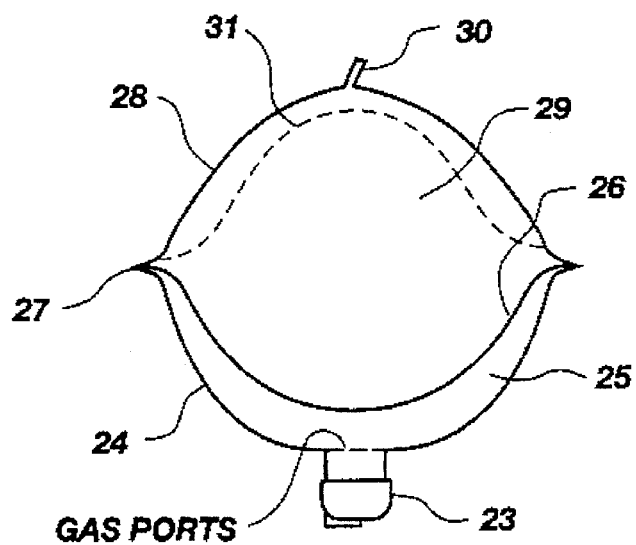
FIG. 3 is a schematic illustration of a fluid dispensing apparatus employing a gas-generating cell of the type illustrated in FIG. 2.

FIG. 3 is an illustration of a fluid dispensing apparatus employing a gas-generating cell 23 of the type illustrated in FIG. 2.

The cell 23 is fixed to a gas shell 24, which is preferably rigid and made of metal, plastic or similar material. The exhaust or gas ports 19 of the gas-generating cell communicate with a gas chamber 25, which is filled with gas, over time, from the gas-generating device 23. A flexible diaphragm 26 forms a gas-tight seal about the rim 27 of the gas shell to form one portion of the gas chamber 25. A fluid shell 28 is also attached to rim 27 to form a fluid reservoir 29. An outlet vent 30 provides a discharge opening for fluid contained within the fluid reservoir, which is forced out of the reservoir by gas pressure within the gas chamber 25 which presses the flexible diaphragm into the fluid reservoir until the diaphragm is completely flexed or distended, as illustrated at position 31. The use of a diaphragm to discharge a fluid reservoir for somewhat similar purposes and in a somewhat similar manner is illustrated in Richter, supra. The disclosure of said patent relating to fluid dispensing is incorporated heroin by reference.

A particular feature of the instant invention is that it is completely self-contained, i.e. no exposure to the outside environment by the electrochemical cell is required. For example, oxygen from the atmosphere is required at the cathode of Maget type devices (see U.S. Pat. No. 4,552,698) to react with the cathode to form water. Without this oxygen, water would not be formed at the cathode and would not be present to permeate the membrane and supply $H_2O$ at the anode.

An aspect of Maget-type and similar devices employing Nation membranes is that they are affected by humidity, thus while the cathode compartment must be open to the atmosphere to permit oxygen to be available, moisture in the atmosphere will also be present at the cathode. Alteration of the moisture content, i.e. concentration in the membrane alters the conductivity of the membrane and thus changes the rate of oxygen generated, which also alters the rate at which dispensed fluid would be delivered.

Fluid delivery devices, such as micro delivery devices to deliver medicines, etc. require accurate flow rates over extended periods of times. Thus, a variation in flow rate with humidity is not a desirable feature of such a device.

The self-contained device of the instant invention is independent of atmospheric conditions and thus delivers a constant flow rate of $O_2$ and, consequently, delivers a constant rate of dispensed fluid whether the device is used in humid or arid climates or environments. For example, buildings cooled by evaporative air conditioners are humid while buildings cooled by refrigerated air conditioning have cool, drier air.

Sealing of the device can be very simple inasmuch as the power supply (battery) may be external to the gas-generating cell. The cell can be completely contained within a canister, similar to a button cell battery.

Although the invention has been illustrated hereinabove with a decomposable metal oxide, namely $Ag_2O$, as the principal cathode material, other chemical compounds containing oxygen which will electrochemically react at a cathode to produce water molecules when in tile presence of protons may be used. The chemical compounds should preferably form water while consuming protons and not produce hydrogen at the cathode.

Depending on the conditions the membrane will be either a cation conductor which is permeable to water, and in some cases the membrane may be microporous having permeability to ions and water. A microporous membrane may be used if the back-reaction between the chemical compound in tile cathode and oxygen is very slow. Preferably, however, the membrane is a undirectional transporter of ions only when under the influence of a voltage differential.

Usually the electrochemical reactions must be driven by a voltage source such as a battery, although in some cases the reactions are self driving and require only an electrical circuit to be completed for the flow of electrons between the cathode and anode, other than through the separator;

Michael Hull and Herbert James in "Why Alkaline Cells Leak," J. Electrochem. Soc., March 1977, describe the problem encountered with electrochemical cells which utilize alkaline electrolytes. Leakage of the caustic electrolyte is very difficult to prevent at the cathode. "One driving force for this phenomenon is the production of $OH^-$ ions arising from the electrochemical reduction of oxygen and/or the evolution of hydrogen occurring in a thin reaction zone above the observed electrolyte meniscus." Hydroxyl ions are produced through reactions 3 or 4 below:

3) $O_2+2H_2+4e^{31} \rightarrow 4\ OH^-$

4) $2H_2O+2e^- 2OH^-+H_2$

In both cases, the reactants may come from the vapor phase. As the hydroxyl ions are formed above the meniscus, electrolyte cations electromigrate toward them to maintain electroneutrality. Then since the alkaline salt is hygroscopic, moisture is absorbed. The net result is creepage of electrolyte along the negatively polarized electrode. Unlike the case of alkaline electrolytes, in the cathode reaction described in reaction 1 above, where acidic or neutral electrolyte is utilized, all reactants come from the liquid or solid phase rather than the vapor phase. Thus the tendency to form products above the liquid/electrode meniscus does not exist. Therefore, the cells in the present invention are less difficult to seal compared to cells with alkaline electrolytes.

EXAMPLES UTILIZING A CATION CONDUCTING MEMBRANE:

Cathode reactants are mixed with a proton conducting material or liquid such as weak sulfuric acid:

1) Cathode material—$Ag_2O$
   Cathode reaction:
   $Ag_2O+2H^++2e^- \rightarrow 2Ag+H_2O$
   Anode reaction:
   $H_2O \rightarrow \frac{1}{2}O_2+2H^++2e^-$
   Overall reaction:
   $Ag_2O \rightarrow Ag+\frac{1}{2}O_2\ E^0=-0.06V$ These reactions together require an applied voltage to proceed. Water is produced at the cathode, permeates through the membrane under a concentration gradient and is consumed at the anode at the same rate at which is it produced. Likewise, protons are produced at the anode, migrate through the membrane under a voltage gradient, and are consumed at the same rate at which they are produced. The weak acid assists in proton conduction.

Undesirable competing cm bode reaction:
$2H^++2e^- \rightarrow H_2$

The undesirable competing cathode reaction in which hydrogen gas is evolved thermodynamically does not proceed in preference to the desired cathode reaction; however, at high cell voltages, the competing reaction will occur. Desirable oxygen release rates can be achieved without high cell voltages if the cell design is one which limits the current density by adjusting the separator/electrode areas. Preferable voltages and preferable current densities will be dependent on the actual membranes and electrodes utilized. The production of hydrogen was not a problem with the cells described in the examples below. Cells maintained in such a range have negligible hydrogen production in the cathode chamber.

PROTON TRANSPORT EXAMPLES

Other posible cell choices with acidic electrolytes include the following:

| Cathode | Anode | Overall | $E^0(V)$ |
|---|---|---|---|
| $Ag_2O + 2H^+ + 2e^- \rightarrow 2Ag + H_2O$ | $H_2O \rightarrow \frac{1}{2}O_2 + 2H^+ + 2e^-$ | $Ag_2O \rightarrow Ag + \frac{1}{2}O_2$ | −0.06 |
| $AgO + 2H^+ + 2e^- \rightarrow Ag + H_2O$ | $H_2O \rightarrow \frac{1}{2}o_2 + 2H^+ + 2e^-$ | $AgO \rightarrow Ag + \frac{1}{2}o_2$ | +0.07 |
| $\frac{1}{2}PbO_2 + 2H^+ + 2e^- \rightarrow \frac{1}{2}Pb + H_2O$ | $H_2O \rightarrow \frac{1}{2}O_2 + 2H^+ + 2e^-$ | $\frac{1}{2}PbO_2 \rightarrow \frac{1}{2}Pb + \frac{1}{2}O_2$ | −0.56 |
| $Cu_2O + 2H^+ + 2e^- \rightarrow 2Cu + H_2O$ | $H_2O \rightarrow \frac{1}{2}O_2 + 2H^+ + 2e^-$ | $Cu_2O \rightarrow 2Cu + \frac{1}{2}O_2$ | −0.76 |
| $CuO + 2H^+ + 2e^- \rightarrow Cu + H_2O$ | $H_2O \rightarrow \frac{1}{2}O_2 + 2H^+ + 2e^-$ | $CuO \rightarrow Cu + \frac{1}{2}O_2$ | −0.67 |

WATER CONSUMING EXAMPLES

In addition to the most preferred materials, other cathode materials may be utilized which are less desirable in that the device must be packaged with water to be consumed. In this category, current is maintained and oxygen is released at a steady rate, but only as long as there is an excess of water available to perpetuate the process.

Although these cells consume water, the amount of water to be consumed can easily be predetermined and packaged as part of the cathode, or in the oxygen chamber from which the water may be imbibed at the anode.

Both types of cells, those which are net consumers of water and those which are not, can be completely sealed from the environment so that water will not be lost to the environment in dry conditions. Since the conductivity of many ion conducting membranes are functions of water content, being sealed eliminates ambient humidity as a variable. Also the device could be exposed to precipitation without a significant effect.

A gel forming material such as carboxymethyl cellulose may be desirable to hold the cathode material in place while manufacturing, but it is not essential.

EXAMPLE 1

Figure 4:
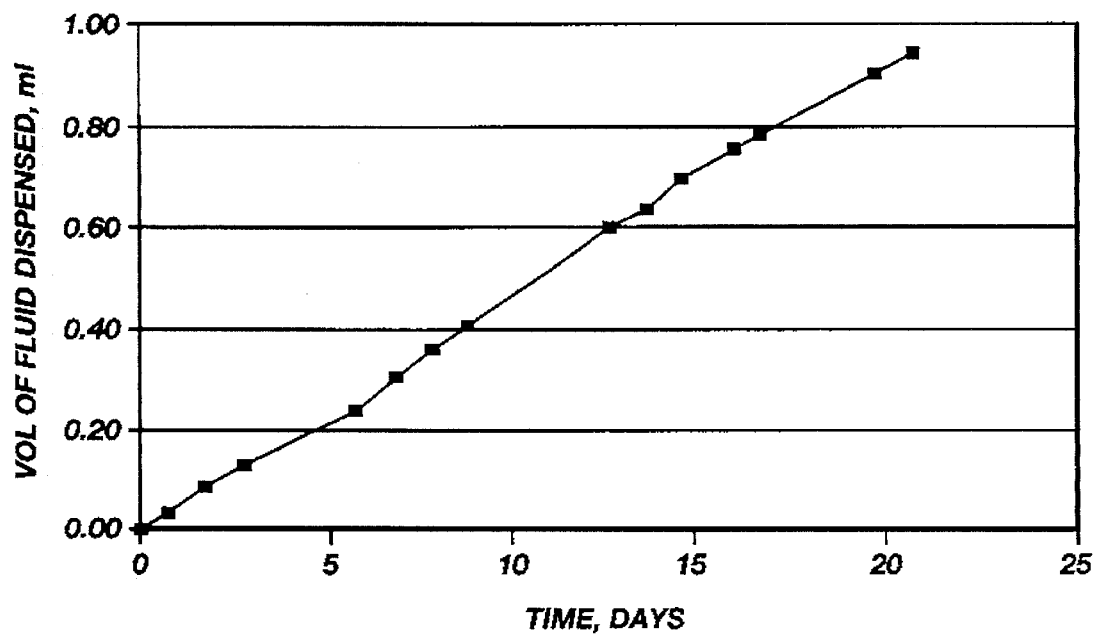
FIG. 4 is a Fluid Dispensing Rate Graph for the system of example 1.

An anode of about 0.2 square centimeters was adhered to a perfluorinated sulfonic membrane, the membrane was Nation 115 from DuPont. The electrode consisted approximately of 11% $RuO_2$ powder, 60% graphite powder, and 29% 1100 equivalent weight Nation. A cathode paste was prepared which consisted of 81% CuO powder and 19% weak (1%) sulfuric acid solution. The paste was placed into a cathode cavity shown schematically in FIG. 1. The membrane/anode composite was placed in contact with the cathode paste such that the cathode and anode were on opposite sides. Total membrane area was about 1 square centimeter. The cell assembly was attached to a reservoir assembly where the fluid sack was filled with water. The cell was driven with a silver oxide battery through a 16000Ω resistor. The amount of fluid dispensed was determined gravimetrically. A plot of the fluid dispensed over time is shown in FIG. 4. The plot shows that the fluid was dispensed at a nearly constant rate.

EXAMPLE 2

Figure 5:
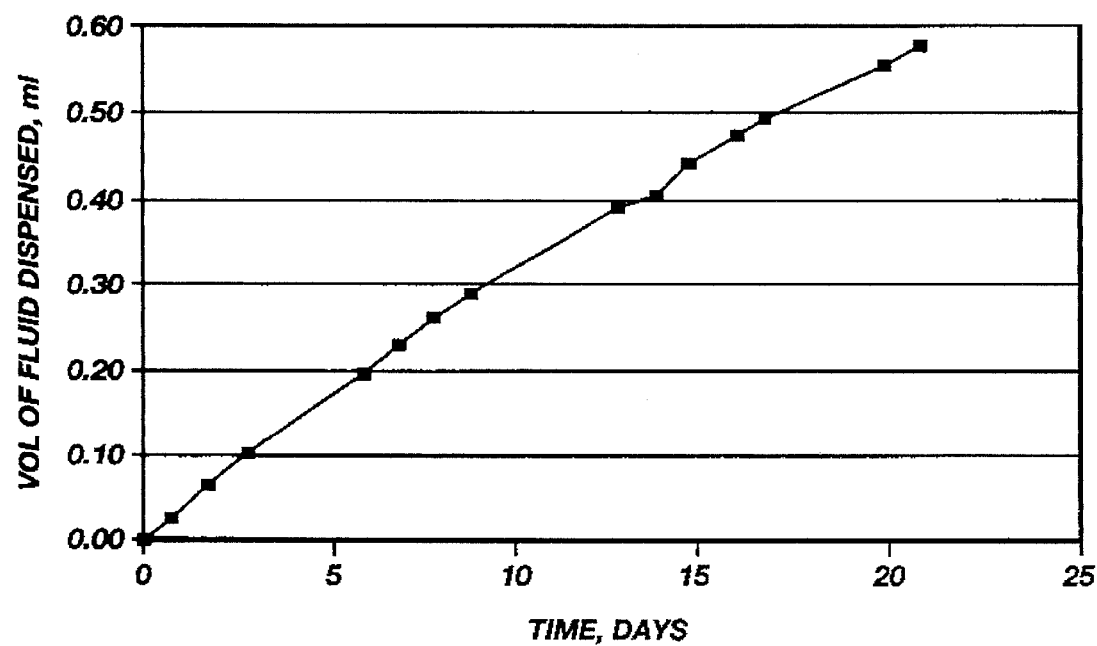
FIG. 5 is a Fluid Dispensing Rate Graph for the system of example 2.

An anode of about 0.2 square centimeters was adhered to a perfluorinated sulfonic membrane, the membrane was Nation 115 from DuPont. The electrode consisted approximately of 11% $RuO_2$ powder, 60% graphite powder, and 29% 1100 equivalent weight Nation. A cathode paste was prepared which consisted of 69% $Ag_2O$ powder and 31% weak (1%) sulfuric acid solution. The paste was placed into a cathode cavity shown schematically in FIG. 1. The membrane/anode composite was placed in contact with the cathode paste such that the cathode and anode were on opposite sides. Total membrane area was about 1 square centimeter. The cell assembly was attached to a reservoir assembly where the fluid sack was filled with water. The cell was driven with a silver oxide battery through a 16000Ω resistor. The amount of fluid dispensed was determined gravimetrically. A plot of the fluid dispensed over time is shown in FIG. 5. The plot shows that the fluid was dispensed at a nearly constant rate.

EXAMPLE 3

An anode of about 0.2 square centimeters was adhered to a perfluorinated sulfonic membrane, the membrane was Nation 115 from DuPont. The electrode consisted approximately of 11% $RuO_2$ powder, 60% graphite powder, and 29% 1100 equivalent weight Nation. A cathode paste was prepared which consisted of 33% $Ag_3O$ powder, 33% carbon powder and 33% weak (1%) sulfuric acid solution. The paste was placed into a cathode cavity shown schematically in FIG. 6. The membrane/anode composite was placed in contact with the cathode paste such that the cathode and anode were on opposite sides. Total membrane area was about 1 square centimeter. The cell assembly was attached to a reservoir assembly where the fluid sack was filled with water. The cell was driven with a silver oxide battery through a 16000Ω resistor. The amount of fluid dispensed was determined gravimetrically. A plot of the fluid dispensed over time is shown in FIG. 1. The plot shows that the fluid was dispensed at a nearly constant rate.

EXAMPLE 4

Figure 7:
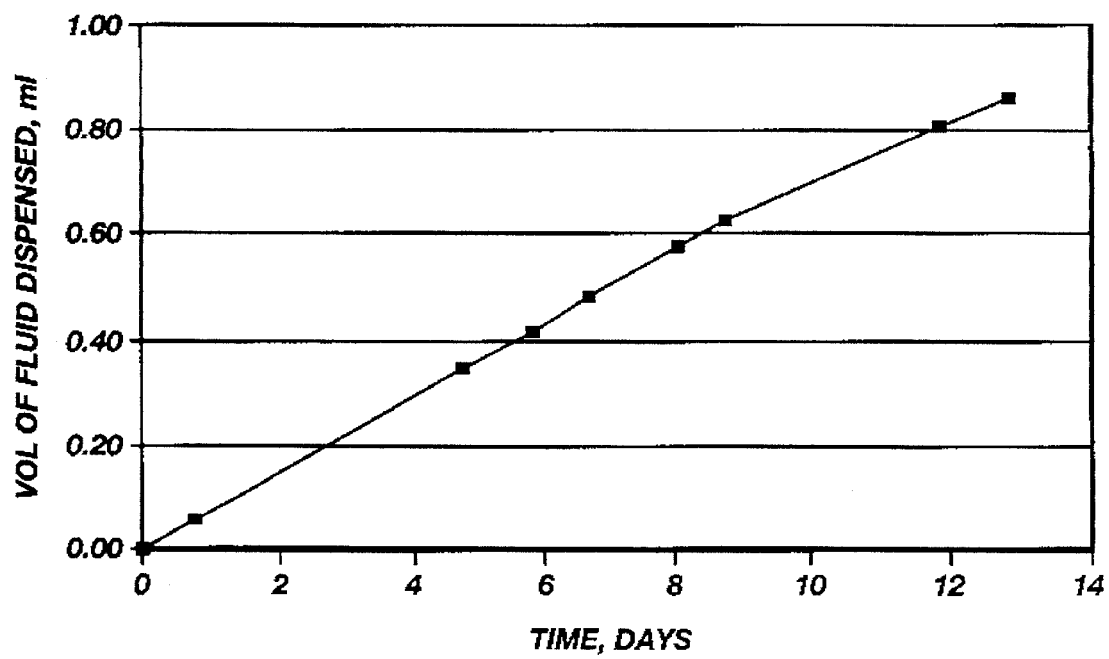
FIG. 7 is a Fluid Dispensing Rate Graph for the system of example 4.

An anode of about 0.2 square centimeters was adhered to a glass fiber separator called Ultipor by Pall RAI. The electrode consisted approximately of 11% $RuO_2$ powder, 60% graphite powder, and 29% 1100 equivalent weight Nation. A cathode paste was prepared which consisted of 81% CuO powder and 19% weak (1%) sulfuric acid solution. The paste was placed into a cathode cavity shown schematically in FIG. 1. The membrane/anode composite was placed in contact with the cathode paste such that the cathode and anode were on opposite sides. Total membrane area was about 1 square centimeter. The cell assembly was attached to a reservoir assembly where the fluid sack was filled with water. The cell was driven with a silver oxide battery through a 1600Ω resistor. The amount of fluid dispensed was determined gravimetrically. A plot of the fluid dispensed over time is shown in FIG. 7. The plot shows that the fluid was dispensed at a nearly constant rate.

What is claimed is:

1. An electrochemical cell capable of generating a gas when said cell contains a proton conducting electrolyte comprising:

a sealed cathode compartment containing a proton conducting electrolyte comprising water and a metal oxide compound consisting of an electrochemically reducible metal oxide;

a cathode member associated with said cathode compartment;

an anode compartment having a gas outlet port and an anode member;

a separator between said anode and cathode compartments, said separator being pervious to water molecules and being a proton conductor when exposed to a proton conducting electrolyte; and a power supply having its negative pole communicating with said cathode member and its positive pole communicating with said anode member.

2. The cell of claim 1, wherein said metal oxide is an oxide of Ag, Pb, Cu, Zn or Bi.

3. The cell of claim 1, wherein said separator is a proton-conducting, sulfonated polymer.

4. The cell of claim 1, wherein said proton conducting electrolyte is an aqueous acid, aqueous salt solution, or water.

5. The cell of claim 1, wherein said proton conducting electrolyte contains a gelling agent.

6. The cell of claim 1, wherein said separator is a hydrophilic microporous polymer sheet containing said electrolyte.

7. The cell of claim 1, wherein said cathode compartment contains dispersed, solid-polymer electrolyte in addition to said water and reducible metal oxide.

8. The cell of claim 1, wherein said separator is a hydrophilic microporous ceramic or organic membrane containing said electrolyte as water or acid.

9. An electrically powered, self-contained, fluid-dispensing pump comprising:

an electrochemical cell capable of generating a gas when said cell contains a proton conducting electrolyte comprising:

a sealed cathode compartment containing water and a metal oxide compound consisting of an electrochemically reducible metal oxide;

a cathode member associated with said cathode compartment;

an anode compartment having a gas outlet port and an anode member;

a separator between said anode and cathode compartments, said separator being pervious to water molecules and being a proton conductor when exposed to a proton conducting electrolyte; and a power supply having its negative pole communicating with said cathode member and its positive pole communicating with said anode member;

a fluid containing chamber having fluid discharge outlet and a gas inlet; and duct means providing gas communication between the anode outlet port of said cell and the gas inlet of said chamber.

10. The fluid dispensing pump of claim 9, wherein said chamber contains a diaphragm which separates said gas inlet from said fluid discharge outlet.

* * * * *

UNITED STATES PATENT AND TRADEMARK OFFICE
CERTIFICATE OF CORRECTION

PATENT NO. : 5,538,605
DATED : July 23, 1996
INVENTOR(S) : Joshi et al.

It is certified that error appears in the above-indentified patent and that said Letters Patent is hereby corrected as shown below:

In col. 1, line 34, delete the semicolon after "chambers";

In col. 1, line 38, change the comma after "brane" to a semicolon;

In col. 1, line 41, change "catalyst" to --catalysts--;

In col. 1, line 55, change the comma after "wall" to a semicolon;

In col. 2, line 6, change the comma after "fluid" to a semicolon;

In col. 2, line 30, change "oxygens" to --oxygen--;

In col. 2, line 36, change "seals" to --seal;--;

In col. 2, line 48, change "fiction" to --function--;

In col. 2, line 61, change "frown" to --from--;

In col. 3, line 11, after "of" (second occurrence) insert --an--;

In col. 3, line 57, change "Nation" to --Nafion--;

In col. 4, line 16, change "13" to --16--;

In col. 5, line 3, change "electrocatalyst" to --electrocatalysts--;

In col. 5, line 31, insert a comma after "shown" and change "with" to --which--;

UNITED STATES PATENT AND TRADEMARK OFFICE
CERTIFICATE OF CORRECTION

PATENT NO. : 5,538,605
DATED : July 23, 1996
INVENTOR(S) : Joshi et al.

It is certified that error appears in the above-indentified patent and that said Letters Patent is hereby corrected as shown below:

In col. 6, line 14, change "heroin" to --herein--;

In col. 6, line 25, change "Nation" to --Nafion--, change the comma after "humidity" to a semicolon, and insert a comma after "thus";

In col. 6, line 53, change "tile" to --the--;

In col. 6, line 61, change "tile" to --the--;

In col. 6, line 63, change "undirectional" to --unidirectional--;

In col. 7, line 2, change the semicolon to a period;

In col. 7, line 23, in the equation change "$2H_2$" to --$2H_2O$-- and "$4e^{31}$" to --$4e^-$--;

In col. 7, line 24, in the equation after "$2e^-$" insert -- $\rightarrow$ --;

In col. 7, line 59, change "cm bode" to --cathode--;

In col. 8, in the table under the heading "Anode," line two, change $\frac{1}{2}o_2$ to --$\frac{1}{2}O_2$--;

In col. 8, in the table under the heading "Overall," line two, change $\frac{1}{2}o_2$ to --$\frac{1}{2}O_2$--;

In col. 8, line 50, change "Nation" to --Nafion--;

UNITED STATES PATENT AND TRADEMARK OFFICE
CERTIFICATE OF CORRECTION

PATENT NO. : 5,538,605
DATED : July 23, 1996
INVENTOR(S) : Joshi et al.

Figure 6:
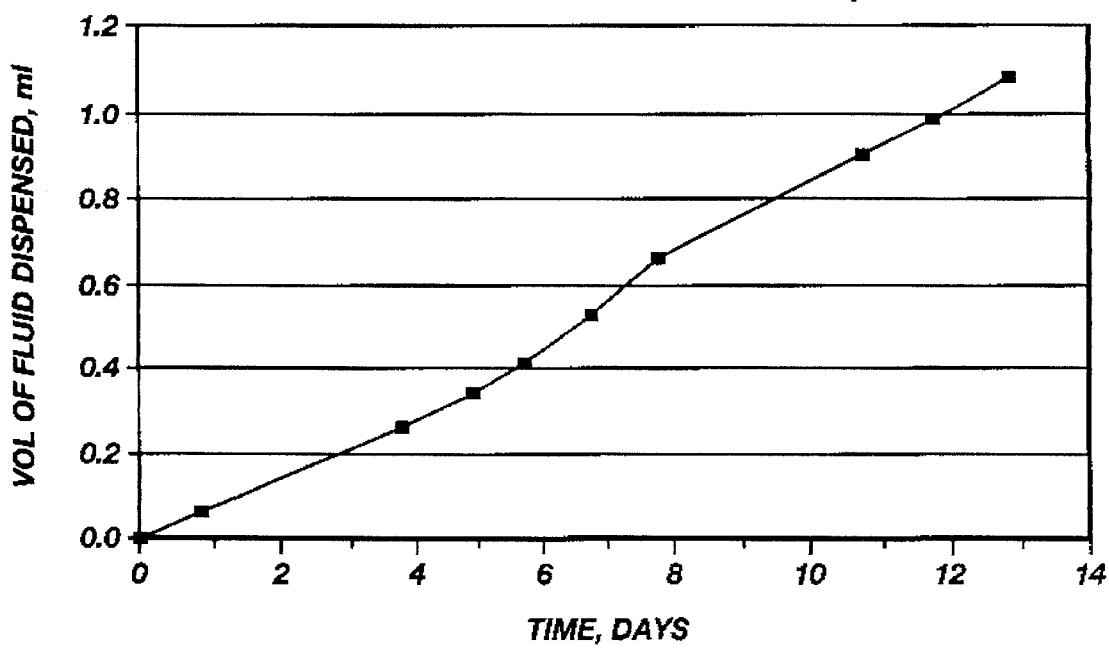
FIG. 6 is a Fluid Dispensing Rate Graph for the system of example 3.

It is certified that error appears in the above-indentified patent and that said Letters Patent is hereby corrected as shown below:

In col. 9, line 1, change "Nation" to --Nafion--;

In col. 9, line 3, change "Nation" to --Nafion--;

In col. 9, line 21, change "Nation" to --Nafion--;

In col. 9, line 23, change "Nation" to --Nafion--;

In col. 9, line 24, change "$Ag_3O$" to --$Ag_2O$--;

In col. 9, line 35, change "FIG. 1" to --FIG. 6--;

In col. 9, line 44, change "Nation" to --Nafion--;

In col. 9, line 56, change the comma at the end of the line to a period; and

In col. 10, line 54, delete "a fluid containing chamber" and insert therefor --a chamber for fluid-- and insert --a-- after "having".

Signed and Sealed this

Seventeenth Day of December, 1996

Attest:

BRUCE LEHMAN

Attesting Officer

Commissioner of Patents and Trademarks